United States Patent
Lee et al.

(10) Patent No.: US 9,304,093 B2
(45) Date of Patent: Apr. 5, 2016

(54) DEVICE AND METHOD FOR MEASURING DYNAMIC THERMAL CONDUCTIVITY OF MICRO-STRUCTURE FLUID

(75) Inventors: Wook-Hyun Lee, Daejeon (KR);
Seong-Ryong Park, Daejeon (KR);
Chong-Youp Kim, Daejeon (KR);
Seok-Won Kim, Seoul (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 520 days.

(21) Appl. No.: 13/814,079

(22) PCT Filed: Aug. 12, 2011

(86) PCT No.: PCT/KR2011/005926
§ 371 (c)(1),
(2), (4) Date: Feb. 4, 2013

(87) PCT Pub. No.: WO2012/021021
PCT Pub. Date: Feb. 16, 2012

(65) Prior Publication Data
US 2013/0128916 A1 May 23, 2013

(30) Foreign Application Priority Data
Aug. 12, 2010 (KR) .................. 10-2010-0078003

(51) Int. Cl.
*G01N 25/18* (2006.01)
(52) U.S. Cl.
CPC ..................................... *G01N 25/18* (2013.01)
(58) Field of Classification Search
CPC .................................................... G01N 25/18
See application file for complete search history.

(56) References Cited

U.S. PATENT DOCUMENTS

2010/0018332 A1*  1/2010  Moriya et al. ............... 73/865.8
2010/0136795 A1*  6/2010  Honma ......................... 438/758

FOREIGN PATENT DOCUMENTS

JP  2000055846  2/2000
JP  2001021512  1/2001

(Continued)

OTHER PUBLICATIONS

Kim, Bong-Hun, "A Study on the Thermal Conductivity of Carbon-Nanotube Nanofluids", Korean Journal of Air-Conditioning and Refrigeration Engineering vol. 19, pp. 275-283, Aug. 18, 2007.

(Continued)

*Primary Examiner* — Lisa Caputo
*Assistant Examiner* — Nasir U Ahmed
(74) *Attorney, Agent, or Firm* — Westman, Champlin & Koehler, P.A.; Amanda M. Prose

(57) ABSTRACT

A device and method for measuring dynamic thermal conductivity of micro-structure fluid. The device includes an upper fixing plate (110a) and a lower fixing plate (110b) which are vertically spaced apart from each other, a lower body (150b) which defines a side surface of a separation space formed between the upper fixing plate and the lower fixing plate, a rotating plate (120) which is disposed in the separation space in such a way that gaps are respectively formed among the rotating plate and the upper and lower fixing plates, a shaft (140) which passes through the upper fixing plate and is coupled to the rotating plate, a heater which installed on an upper portion of the upper fixing plate, and thermocouples (118a) and (118b) which are respectively installed in the upper and lower fixing plates.

8 Claims, 9 Drawing Sheets

(56) References Cited

FOREIGN PATENT DOCUMENTS

| | | |
|---|---|---|
| JP | 2004061302 | 2/2004 |
| KR | 200334651 | 11/2003 |
| KR | 100791829 | 12/2007 |

OTHER PUBLICATIONS

International Search Report dated Mar. 26, 2012 from International Patent Application No. PCT/KR2011/005926.
International Written Opinion dated Mar. 26, 2012 from International Patent Application No. PCT/KR2011/005926.

* cited by examiner

DEVICE AND METHOD FOR MEASURING DYNAMIC THERMAL CONDUCTIVITY OF MICRO-STRUCTURE FLUID

CROSS-REFERENCE TO RELATED APPLICATION(S)

This Application is a 371 National Stage Application of International Application No. PCT/KR2011/005926, filed on Aug. 12, 2011, published as International Publication No. WO2012/021021, which claims priority to Korean Patent Application No. 10-2010-0078003, filed on Aug. 12, 2010, the contents of which are incorporated by reference in their entireties.

TECHNICAL FIELD

The present invention relates, in general, to devices and methods of measuring dynamic thermal conductivity of micro-structure fluid and, more particularly, to a device and method which can measure dynamic thermal conductivity of micro-structure fluid depending on the shear rate under steady-state temperature conditions even if the amount of micro-structure fluid is small, and which can prevent convection resulting from centrifugal force, concentration and temperature gradients and minimize a heat loss, thereby making it possible to accurately measure the dynamic thermal conductivity of the micro-structure fluid.

BACKGROUND ART

Generally, micro-structure fluid refers to fluid having a micro-structure, for example, a suspension in which solid particles are dispersed in liquid, an emulsion which is a mixture of two or more kinds of liquids, and a polymer solution. The micro-structure in fluid sensitively varies depending on shear stress applied to the fluid. Thus, when fluid flows, thermal transfer characteristics of the fluid are expected to be varied. Because the thermal transfer characteristics of the micro-structure fluid make it sensitive to temperature, when the thermal conductivity of the micro-structure fluid is measured, an environment for creating the steady-state temperature conditions is required.

Meanwhile, a hot-wire method which measures thermal conductivity under unsteady-state conditions is widely used because it can comparatively simply measure the thermal conductivity of a fluid or a solid in a short time. However, in the hot-wire method, the measurement is conducted in such a way that a probe is immersed into fluid. Hence, the hot-wire method is unsuited for the purpose of measuring the thermal conductivity of micro-structure fluid. For example, when thermal conductivity of a fluid, such as a suspension, an emulsion or a polymer solution, having a micro-structure is measured, heat is applied to the surroundings of the probe (hot wire) so that solid-phase concentration gradients are formed. The concentration gradients cause convection resulting from density difference. Thereby, the thermal conductivity cannot be accurately measured.

DISCLOSURE

Technical Problem

Accordingly, the present invention has been made keeping in mind the above problems occurring in the prior art, and an object of the present invention is to provide a device and method which can measure dynamic thermal conductivity of micro-structure fluid depending on the shear rate under normal temperature conditions even if the amount of micro-structure fluid is small, and which can prevent convection resulting from centrifugal force, concentration and temperature gradients and minimize a heat loss, thereby making it possible to accurately measure the dynamic thermal conductivity of the micro-structure fluid.

Technical Solution

In order to accomplish the above object, in an aspect, the present invention provides a device for measuring dynamic thermal conductivity of micro-structure fluid, including: an upper fixing plate and a lower fixing plate vertically spaced apart from each other; a lower body defining a side surface of a separation space formed between the upper fixing plate and the lower fixing plate; a rotating plate disposed in the separation space in such a way that gaps are respectively formed between the rotating plate and the upper fixing plate and between the rotating plate and the lower fixing plate; a shaft passing through the upper fixing plate, the shaft being coupled to the rotating plate; a heater installed on an upper portion of the upper fixing plate; and thermocouples installed in each of the upper and lower fixing plates.

In the present invention having the above-mentioned construction, when the rotating plate is rotated, the micro-structure fluid loaded in the separation space defined between the upper fixing plate and the lower fixing plate is under a dynamic state. Simultaneously, if the heater is operated and a constant heat flux is applied, the dynamic thermal conductivity of the micro-structure fluid loaded in the separation space can be measured.

Here, side surfaces of the upper and lower fixing plates may be covered with an insulator, and the heater may be disposed in a cap provided with the insulator so that a heat loss can be minimized. Further, a cooling thermoelement and a heat sink may be provided under the lower fixing plate. In this case, under vibrationless conditions, a temperature difference between the upper and lower fixing plates can be developed with minimizing fluctuation, thus making it possible to more accurately measure the thermal conductivity of the micro-structure fluid. Particularly, if the present invention is disposed in an insulation container provided with a heater installed under a lower surface of the container and then the temperature of the device is controlled, a heat loss or heat absorption between the present invention and the outside can be minimized.

In another aspect, the present invention provides a method of measuring dynamic thermal conductivity of micro-structure fluid using the above-stated measuring device.

The method includes: filling the separation space with the micro-structure fluid; operating the heater and developing a temperature difference between the upper fixing plate and the lower fixing plate; rotating the rotating plate so that the micro-structure fluid is under a dynamic state; and measuring the thermal conductivity using temperatures measured by the thermocouples.

Advantageous Effects

In a device and method of measuring dynamic thermal conductivity of micro-structure fluid according to the present invention, even if the amount of micro-structure fluid is comparatively small, the dynamic thermal conductivity of the micro-structure fluid depending on the shear rate under steady-state temperature conditions can be easily measured. In addition, the present invention can prevent convection resulting from centrifugal force, concentration, and temperature gradients, thus minimizing a heat loss, thereby making it possible to accurately measure the dynamic thermal conductivity of the micro-structure fluid.

DESCRIPTION OF THE REFERENCE NUMERALS IN THE DRAWINGS

Figure 1:
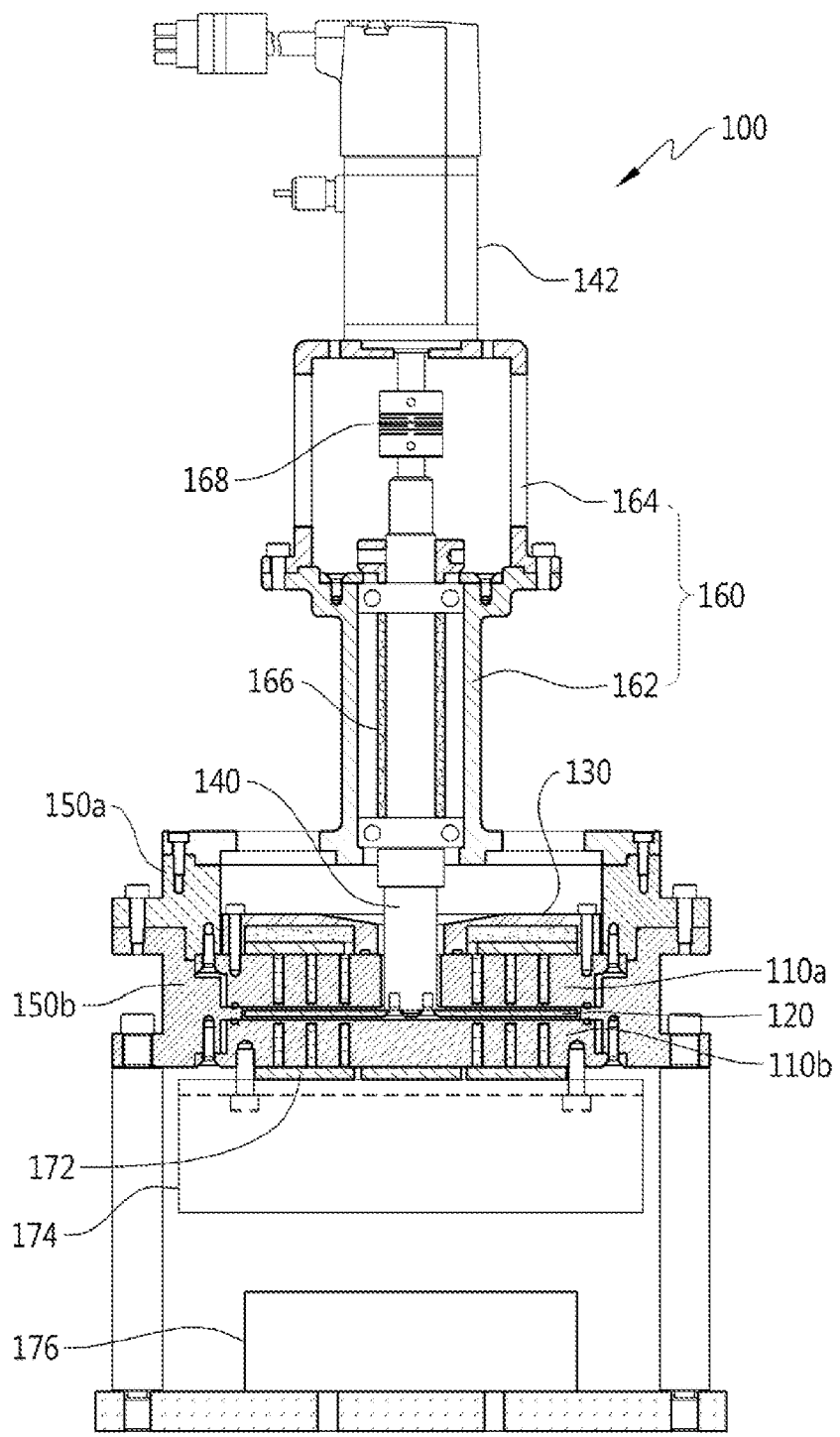
FIG. 1 is a sectional view illustrating a device for measuring dynamic thermal conductivity of a micro-structure fluid, according to a preferred embodiment of the present invention.

100: measuring device 110a: upper fixing plate
110b: lower fixing plate 110c: separation space
120: rotating plate 130: cap
140: shaft 150a: upper body
150b: lower body 160: housing
172: thermoelement 174: heat sink
176: fan Best Mode Hereinafter, an embodiment of the present invention will be described in detail with reference to the attached drawings. Reference should now be made to the drawings, in which the same reference numerals are used throughout the different drawings to designate the same or similar components.

Figure 2:
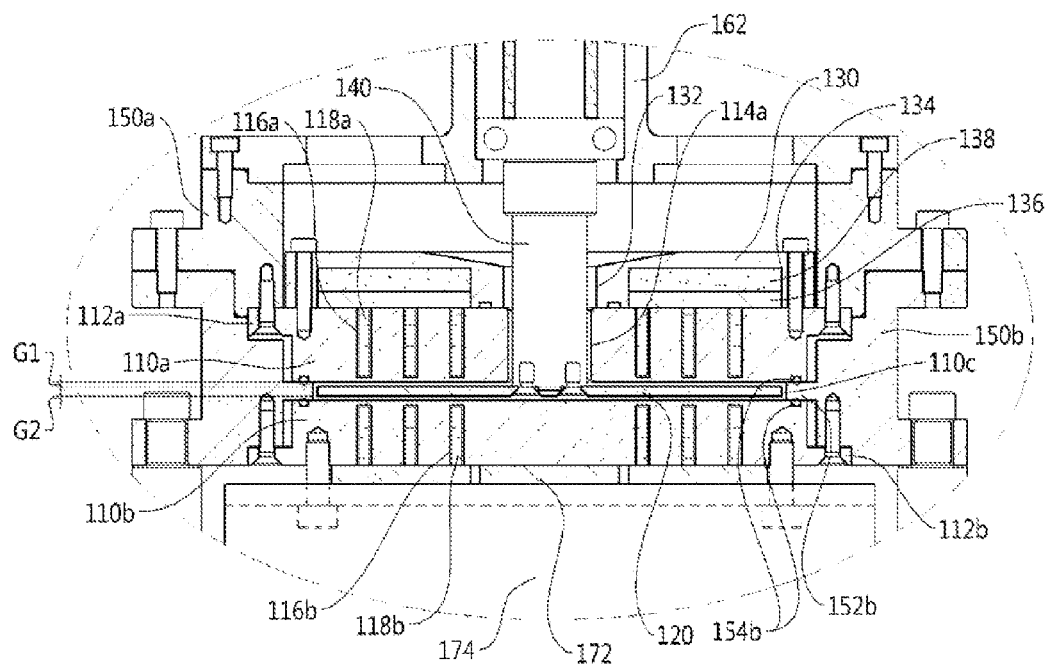
FIG. 2 is an enlarged view of a portion of the FIG. 1.

As shown in FIGS. 1 and 2, a device 100 for measuring dynamic thermal conductivity of micro-structure fluid according to the embodiment of the present invention (hereinafter, referred to as "a measuring device 100") includes an upper fixing plate 110a and a lower fixing plate 110b which are disposed at upper and lower positions spaced apart from each other, a rotating plate 120 which is installed between the upper fixing plate 110a and the lower fixing plate 110b, a cap 130 which is installed on the upper fixing plate 110a, a shaft 140 which is coupled to the rotating plate 120 after passing through the cap 130 and the upper fixing plate 110a, an upper body 150a and a lower body 150b which are installed around the upper fixing plate 110a, the lower fixing plate 110b and the cap 130, and a housing 160 which is installed on the upper body 150a and supports the shaft 140.

Referring to FIG. 2, the upper fixing plate 110a has a disk shape, which includes a flange 112a protruding from a periphery of an upper end thereof. A first through-hole 114a is formed through a central portion of the upper fixing plate 110a so that the shaft 140 is disposed in the first through-hole 114a. Mounting holes 116a are formed in an upper surface of the upper fixing plate 110a. A thermocouple 118a for temperature measurement is installed in each mounting hole 116a.

The lower fixing plate 110b is disposed below the upper fixing plate 110a at a position spaced apart from the upper fixing plate 110a by a predetermined distance so that a separation space 110c is defined between the upper and lower fixing plates 110a and 110b. The lower fixing plate 110b has a shape symmetrical to that of the upper fixing plate 110a based on the separation space 110c, that is, has a disk shape in which a flange 112b protrudes from a periphery of a lower end thereof. Mounting holes 116b in which thermocouples 118b are respectively installed are installed in a lower surface of the lower fixing plate 110b.

Figure 3:
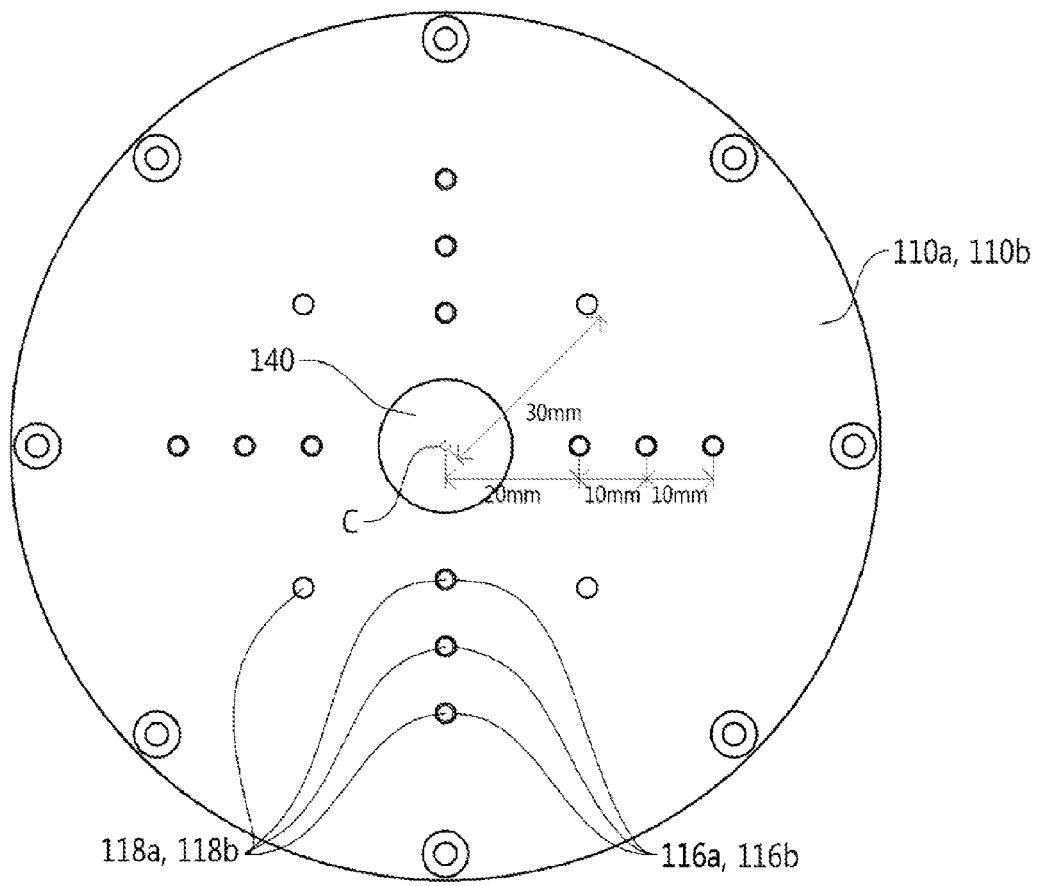
FIG. 3 is a view showing the installation position of thermocouples of the device for measuring the dynamic thermal conductivity of the micro-structure fluid according to the embodiment of FIG. 1.

It is preferable that, as shown in FIG. 3, the thermocouples 118a and 118b which are respectively installed in the mounting holes 116a and 116b of the upper and lower fixing plates 110a and 110b be arranged in radial directions with the first through-hole 114a as the center in order to precisely measure variation in temperature of micro-structure fluid that is loaded in the separation space 110c. More preferably, a plurality of thermocouples 118a or 118b are arranged in a specific direction. For instance, in each of the upper and lower fixing plates 110a and 110b, three thermocouples 118a, 118b which directly measure the temperature of the micro-structure fluid are radially arranged at each of directions of 0°, 90°, 180° and 270° and are disposed at positions spaced apart from a center C of the first through-hole 114a respectively by 20 mm, 30 mm and 40 mm, and a thermocouple 118a, 118b is disposed at each of directions of 45°, 135°, 225° and 315° only at a position spaced apart from the center of the shaft 140 by 30 mm so that the temperature difference between the upper and lower fixing plates 110a and 110b can be measured at a total of four positions.

The rotating plate 120 is a means for enabling the micro-structure fluid that has been loaded in the separation space 110c to be maintained in a dynamic state. In detail, the rotating plate 120 is installed in the separation space 110c formed between the upper fixing plate 110a and the lower fixing plate 110b. The separation space 110c is filled with micro-structure fluid. The rotating plate 120 is disposed such that gaps G1 and G2 are formed between the upper fixing plate 110a and the rotating plate 120 and between the lower fixing plate 110b and the rotating plate 120.

Preferably, a radius of the separation space 110c which is filled with micro-structure fluid is 100 mm, and each of the gaps G1 and G2 among the upper fixing plate 110a, the lower fixing plate 110b and the rotating plate 120 is 0.5 mm. At the above-stated values, when the flow and temperature distribution of micro-structure fluid are checked after the separation space 110c is filled with the micro-structure fluid, the micro-structure fluid can be prevented from fluctuation attributable to convection and remain mostly stable even in an aspect of thermal conduction.

The upper fixing plate 110a, the lower fixing plate 110a and the rotating plate 120 are made of copper which has high thermal conductivity and are coated with corrosion resistant films. The corrosion resistant film is made of glass or gold, and the thickness thereof is preferably 100 μm or less.

As shown in FIG. 2, the cap 130 has a disk shape. The second through-hole 132 is formed through the cap 130, and the shaft 140 is disposed in the second through-hole 132. An insert depression 134 is formed in a lower surface of the cap 130 so that a heater 136 and an insulator 138 are installed in the insert depression 134.

The second through-hole 132, along with the first through-hole 114a of the upper fixing plate 110a, functions as an injection path through which micro-structure fluid is injected into the separation space 110c. For this, the diameter of each of the first and second through-holes 114a and 132 is larger than that of the shaft 140. Particularly, the second through-hole 132 has a funnel-shaped upper end so that micro-structure fluid can be easily injected thereinto.

The heater 136 that is installed in the insert depression 134 functions to heat the micro-structure fluid. The insulator 138 functions to prevent heat generated from the heater 136 from being dissipated to the outside through the cap 130. Preferably, the insulator 138 is disposed on an upper surface of the heater 136 so that heat generated from the heater 136 can be transferred to the micro-structure fluid without a heat loss.

Meanwhile, a cooling thermoelement 172, a heat sink 174 and a fan 176 are provided under a lower surface of the lower fixing plate 110b. The thermoelement 172 is a means for cooling the lower fixing plate 110b using the Peltier effect. The heat sink 174 and the fan 176 function to dissipate heat absorbed by the thermoelement 172 to the outside.

As such, if the lower fixing plate 110b can be cooled by the thermoelement 172, the heat sink 174 and the fan 176, the temperature difference between the upper fixing plate 110a and the lower fixing plate 110b can be easily controlled, and vibration can be reduced compared to a water or air cooling type so that the accuracy in measurement of thermal conductivity can be enhanced.

The shaft 140 has a multi-stepped rod shape. A lower end of the shaft 140 is coupled to the rotating plate 120 after passing through the cap 130 and the upper fixing plate 110a. An upper end of the shaft 140 is connected to a servomotor 142 which controls the rpm of the rotating plate 120.

The lower body 150b forms a sidewall of the separation space 110c defined between the upper fixing plate 110a and the lower fixing plate 110b. The lower body 150b has an annular shape so that it can enclose the peripheries of the upper and lower fixing plates 110a and 110b. A flange 152b protrudes from an inner surface of the lower body 150b and comes into close contact both with a lower surface of the upper fixing plate 110a and with an upper surface of the lower fixing plate 110b. Furthermore, packings 154b are respectively provided on upper and lower surfaces of the flange 152b to reliably seal the separation space 110c.

The upper body 150a functions to press the upper fixing plate 110a onto the flange 152b of the lower body 150b to enhance the airtightness of the separation space 110c.

Referring to FIG. 1, the housing 160 includes a first housing 162 which is installed on an upper surface of the upper body 150a, and a second housing 164 which is provided on an upper end of the upper body 150a. A space ring 166 which supports the shaft 140 is provided in the first housing 162. A coupling 168 which couples the shaft 140 to the servomotor 142 is provided in the second housing 164.

Figure 4:
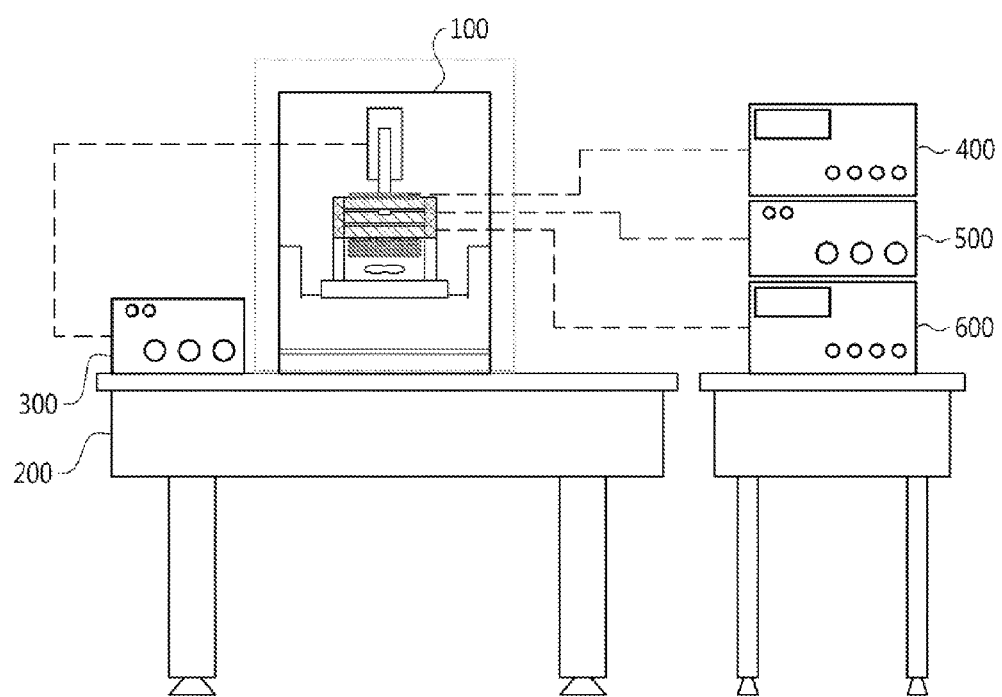
FIG. 4 is a schematic view illustrating a system for measuring dynamic thermal conductivity of micro-structure fluid using the device of the embodiment of FIG. 1.

FIG. 4 is a schematic view illustrating a system for measuring the dynamic thermal conductivity of the micro-structure fluid using the measuring device of the embodiment of the present invention.

The system for measuring the dynamic thermal conductivity of the micro-structure fluid includes the measuring device 100, an optical table 200 which prevents micro-vibration from being applied to the measuring device 100, a servomotor controller 300 which controls the servomotor (142 of FIG. 2) to adjust the rpm of the rotating plate (120 of FIG. 2), a power supply 400 which supplies power to the measuring device 100, a temperature controller 500 which controls the temperature of the heater (136 of FIG. 2), and a data collection device 600 which collects temperature data measured by the thermocouples 118a and 118b.

Figure 5:
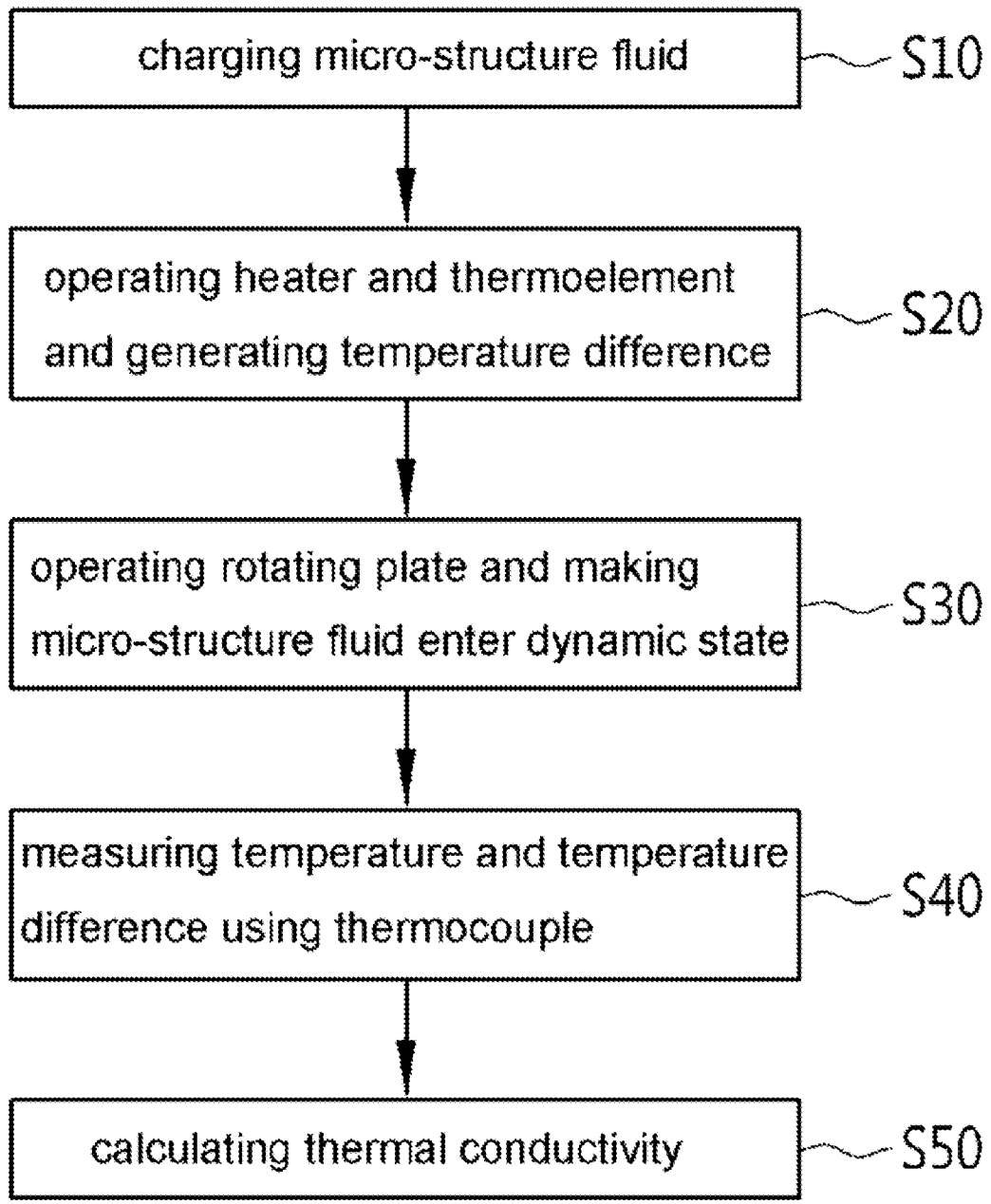
FIG. 5 is a flowchart showing a method of measuring dynamic thermal conductivity of micro-structure fluid using the device of the embodiment of FIG. 1.

A process of measuring the dynamic thermal conductivity of the micro-structure fluid using the measuring device 100 having the above-mentioned construction will be explained with reference to FIG. 5.

First, micro-structure fluid is loaded into the separation space 110c between the upper fixing plate 110a and the lower fixing plate 110b (S10). In detail, the micro-structure fluid can be loaded into the separation space 110c in such a way that after the micro-structure fluid is put into a cylinder (not shown) or the like, it is injected into the separation space 110c through the second through-hole 132 of the cap 130 and the first through-hole 114a of the upper fixing plate 110a.

After the loading of the micro-structure fluid has been completed, the heater 136 is operated to heat the upper fixing plate 110a, and the thermoelement 172 is operated to cool the lower fixing plate 110b, whereby a temperature difference is caused between the upper fixing plate 110a and the lower fixing plate 110b (S20).

Thereafter, the rotating plate 120 is rotated by the operation of the servomotor 142, so that the micro-structure fluid which has been loaded in the separation space 110c is under the dynamic state (S30).

After the micro-structure fluid in the separation space 110c is under the dynamic state through the above-mentioned process, the thermocouples 118a and 118b which are respectively installed in the upper fixing plate 110a and the lower fixing plate 110b measure the temperatures of several portions of the micro-structure fluid and temperature differences therebetween (S40).

Finally, the dynamic thermal conductivity of the micro-structure fluid is calculated using the temperature differences measured by the thermocouples 118a and 118b (S50).

Here, the following Equation 1 can be used to calculate the dynamic thermal conductivity of the micro-structure fluid.

$$Q = -kA\nabla T \approx -kA\frac{\Delta T}{\Delta t} \quad \text{[Equation 1]}$$

$$\Sigma R = \frac{\Delta T}{Q} = \frac{\Delta t}{kA}$$

$$\Sigma R = \left[\frac{K}{W}\right] = 2\left[\frac{t_1}{k_1 \times \frac{\pi}{4} \times D_1^2}\right] + 2\left[\frac{t_2}{k_2 \times \frac{\pi}{4} \times D_1^2}\right] +$$

$$2\left[\frac{t_3}{k_3 \times \frac{\pi}{4} \times D_1^2}\right] + 2\left[\frac{t_3}{k_3 \times \frac{\pi}{4} \times D_2^2}\right] +$$

$$\frac{t_4}{\left[k_1 \times \frac{\pi}{4} \times D_1^2\right] + \left[k_2 \times \frac{\pi}{4} \times (D_1^2 - D_3^2)\right] + \left[k_3 \times \frac{\pi}{4} \times (D_3^2 - D_1^2)\right]}$$

where

Q: heat flux

A: an area of a cross-section perpendicular to a heat flow direction

R: heat resistance $k_1$: a thermal conductivity of the upper fixing plate 110a, the lower fixing plate 110b and the rotating plate 120

$k_2$: a thermal conductivity of the micro-structure fluid $k_3$: a thermal conductivity of the corrosion resistant film $t_1$: a thickness between the bottom of the mounting hole 116a and the lower surface of the upper fixing plate 110a, or a thickness between the top of the mounting hole 116b and the upper surface of the lower fixing plate 110b, in other words, a thickness of a portion of the upper fixing plate 110a or the lower fixing plate 110b in which the mounting hole 116a or 116b is formed $t_2$: a distance between the upper fixing plate 110a and the rotating plate 120, or a distance between the lower fixing plate 110b and the rotating plate 120

$t_3$: a thickness of the corrosion resistant film $t_4$: a distance between the upper fixing plate 110a and the lower fixing plate 110b (a thickness of the separation space 110c)

$D_1$: a diameter of the upper fixing plate 110a and the lower fixing plate 110b $D_2$: a diameter of the rotating plate 120

$D_3$: $D_2 + 2 \times t_3$

As such, if the measuring device according to the present invention is used in measurement, the thermal conductivity of micro-structure fluid depending on the shear rate under steady-state temperature conditions can be easily measured, even if the amount of micro-structure fluid is small. Particularly, convection resulting from concentration and temperature gradients can be prevented, and a heat loss can be minimized, whereby the dynamic thermal conductivity can be accurately measured.

Here, it is preferable that the rpm of the rotating plate 120 which makes the micro-structure fluid to be in the dynamic state be 10 rpm or less. The reason for this is because, if the rpm of the rotating plate 120 is greater than 10 rpm, the micro-structure fluid is vertically mixed by forced convection so that a temperature difference between the upper fixing plate 110a and the lower fixing plate 110b does not occur.

In this embodiment, although the rpm of the rotating plate 120 has been illustrated as being 10 rpm or less, the present invention is not limited to this. For instance, if the diameters of the separation space and the rotating plate are increased and the distance between the lower fixing plate and the rotating plate is reduced, even if the rpm of the rotating plate is even 100 rpm, micro-structure fluid can be prevented from being vertically mixed by forced convection, so the temperature difference between the upper and lower fixing plates can be maintained.

A method of performing a test for measuring the dynamic thermal conductivity of the micro-structure fluid using the above-stated measuring device and method will be described below.

In the test, a suspension which is dispersed in water containing rod type alumina particles (having a diameter of 10 nm and a major axis length of 50 nm; TEM) in which a shear-thinning phenomenon can be comparatively reliably caused was used as micro-structure fluid. Three kinds of suspensions, which respectively had particle concentrations of 1, 3 and 5 volume %, were injected into the measuring device 100, and in the case of each particle concentration, when the rpm of the rotating plate 120 was given as 0, 1 or 5 rpm, the temperature difference was measured. Here, the reason why the rpm of the rotating plate 120 is limited to 10 rpm or less is because, if the rpm of the rotating plate 120 is larger than 10 rpm, as stated above, the suspension is mixed by convection in the longitudinal direction, that is, in the axial direction, of the shaft 140, and thus the temperature difference becomes ambiguous.

Under the above conditions, if it is the assumption that a state in which after heat is applied to the suspension over two hours, variation in temperature of the suspension is reduced be a quasi steady state, the temperature variation in this quasi steady state is ±0.2 K.

Meanwhile, the average thermal conductivity could be calculated during the temperature variation for two hours for which heat is applied to the suspension. The result of this is shown in FIGS. 6 through 8.

Figure 6:
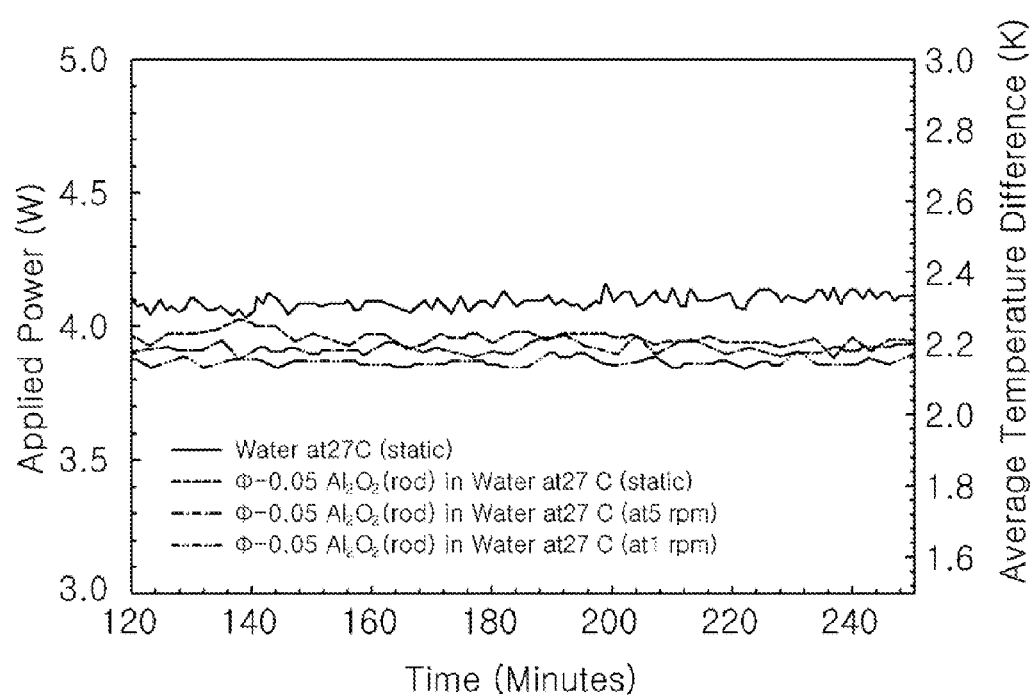
FIG. 6 is a graph showing variation in temperature and heat quantity of a suspension (5.0 volume %) as a function of time according to the rpm of a rotating plate in the measurement of the embodiment of FIG. 1.
Figure 7:
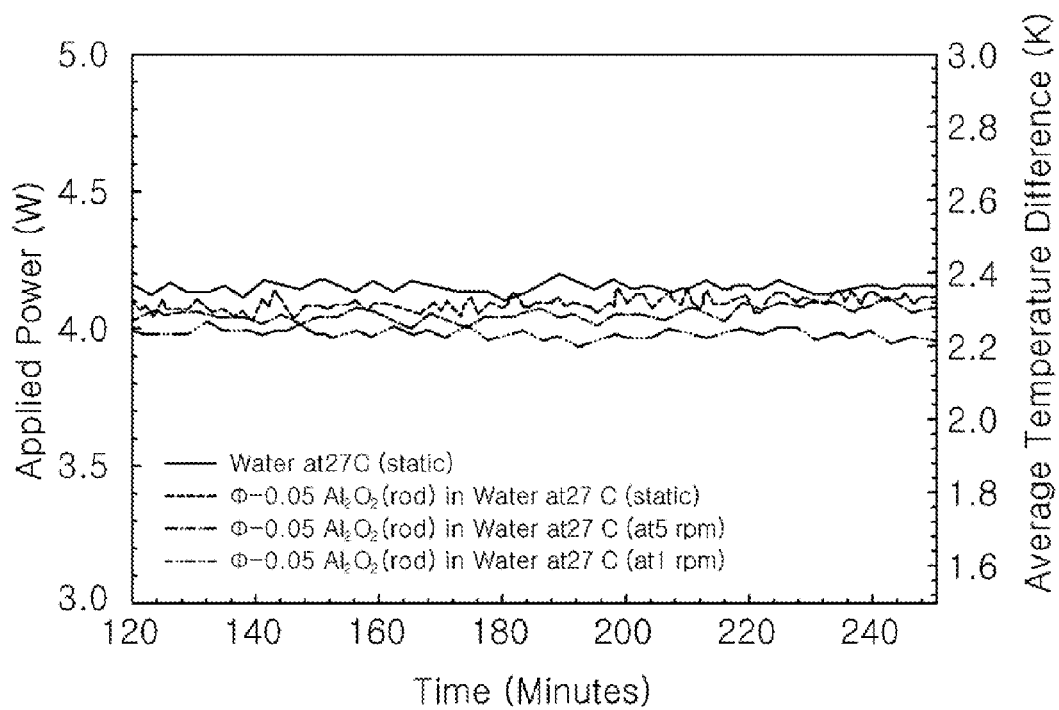
FIG. 7 is a graph showing variation in temperature and heat quantity of a suspension (3.0 volume %) as a function of time according to the rpm of a rotating plate in the measurement of the embodiment of FIG. 1.
Figure 8:
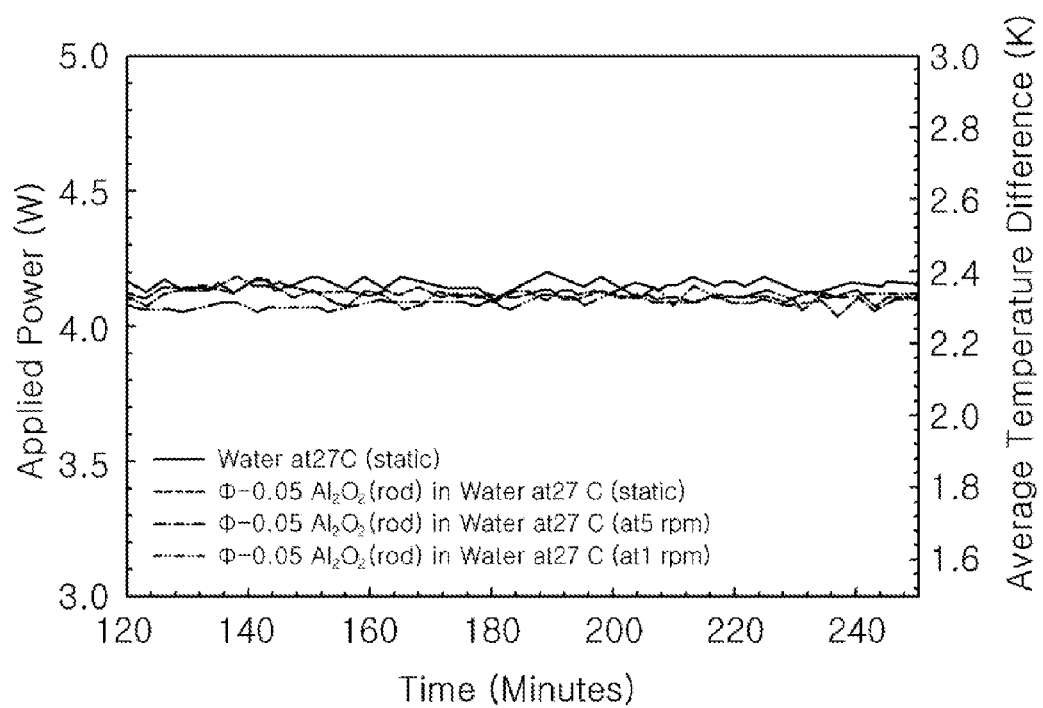
FIG. 8 is a graph showing variation in temperature and heat quantity of a suspension (1.0 volume %) as a function of time according to the rpm of a rotating plate in the measurement of the embodiment of FIG. 1.

Referring to FIGS. 6 through 8, in a static state, the thermal conductivity of a suspension of 5.0 volume % increases by 16.8% compared to that of pure water. However, when the rotating plate 120 is rotated at 5 rpm, a rate of increment in the thermal conductivity of the suspension is 5.32%, in other words, it is reduced to ⅓ of that of the static state. On the other hand, in the case of a suspension of 1.0 volume %, there is little difference in the thermal conductivity between the static state and the dynamic state.

Ultimately, it can be understood that the more the particle concentration increases, the more the micro-structure in the suspension is developed by shear stress applied thereto by the rotating plate 120, whereby heat transfer characteristics are changed.

Figure 9:
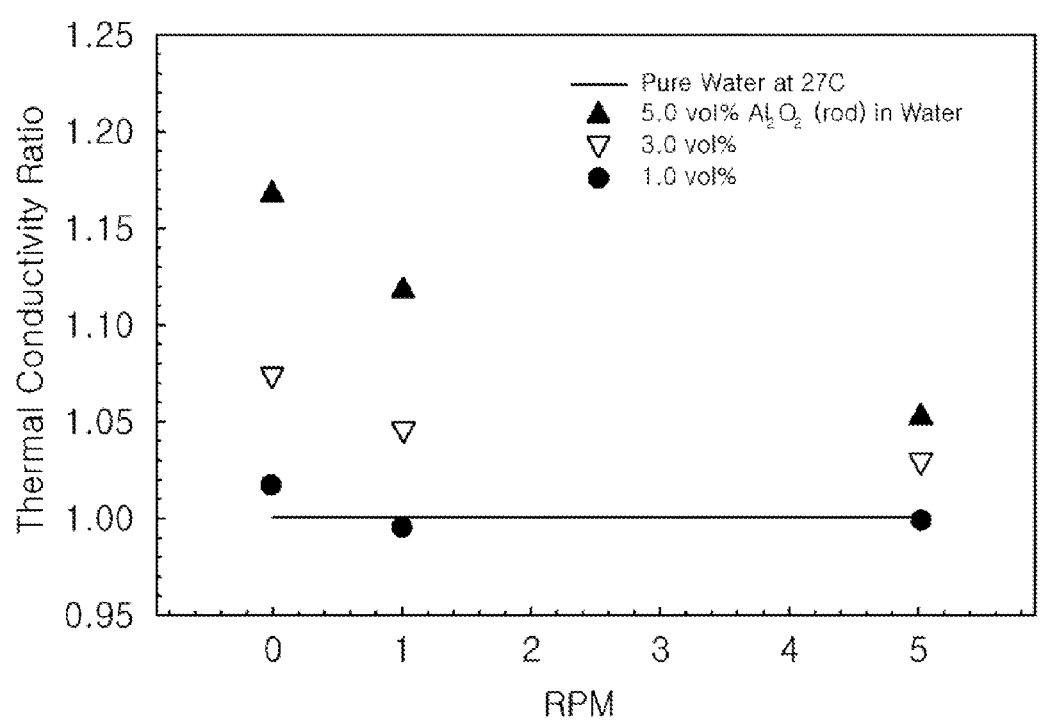
FIG. 9 is a graph showing an increase in thermal conductivity of a suspension as a function of the rpm of the rotating plate according to the concentration of water in the measurement of the embodiment of FIG. 1.

Meanwhile, referring to FIG. 9, it can be understood that as the rpm of the rotating plate 120 increases, the temperature difference of the suspension is increased.

Although the preferred embodiment of the present invention has been disclosed for illustrative purposes, those skilled in the art will appreciate that various modifications, additions and substitutions are possible, without departing from the scope and spirit of the invention as disclosed in the accompanying claims. Therefore, the bounds of the present invention must be defined by the claims rather than the specific embodiment, and all of technical spirits within the equivalent range must also be regarded as falling within the bounds of the present invention.

The invention claimed is:

1. A device for measuring dynamic thermal conductivity of micro-structure fluid, comprising:
    an upper fixing plate and a lower fixing plate vertically spaced apart from each other;
    a lower body defining a side surface of a separation space formed between the upper fixing plate and the lower fixing plate;
    a rotating plate disposed in the separation space in such a way that gaps are respectively formed between the rotating plate and the upper fixing plate and between the rotating plate and the lower fixing plate;
    a shaft passing through the upper fixing plate, the shaft being coupled to the rotating plate;
    a heater installed on an upper portion of the upper fixing plate; and
    a thermocouple installed in each of the upper and lower fixing plates,
    wherein when the rotating plate is rotated, the micro-structure fluid loaded in the separation space is under a dynamic state, and then the thermocouples measure a temperature difference of the micro-structure fluid which is caused by a constant heat flux applied by the heater, thus calculating the dynamic thermal conductivity of the micro-structure fluid.

2. The device for measuring the dynamic thermal conductivity of the micro-structure fluid according to claim 1, further comprising a cooling thermoelement under a lower surface of the lower fixing plate.

3. The device for measuring the dynamic thermal conductivity of the micro-structure fluid according to claim 2, wherein each of the upper fixing plate, the lower fixing plate and the rotating plate is made of copper coated with a corrosion resistant film.

4. The device for measuring the dynamic thermal conductivity of the micro-structure fluid according to claim 3, wherein a thickness of the corrosion resistant film is 100 μm or less.

5. The device for measuring the dynamic thermal conductivity of the micro-structure fluid according to claim 4, wherein a flange is provided on an inner side surface of the lower body, and the upper fixing plate and the lower fixing plate are respectively coupled to upper and lower surface of the flange.

6. The device for measuring the dynamic thermal conductivity of the micro-structure fluid according to claim 1, wherein a radius of the separation space ranges from 20 mm to 200 mm, and the gap between the upper fixing plate and the rotating plate and the gap between the lower fixing plate and the rotating plate range from 0.1 mm to 1.0 mm.

7. A method of measuring dynamic thermal conductivity of micro-structure fluid using the device according to claim 1, the method comprising:
    filling the separation space with the micro-structure fluid;
    operating the heater and generating a temperature difference between the upper fixing plate and the lower fixing plate;
    rotating the rotating plate so that the micro-structure fluid is under a dynamic state; and
    measuring the thermal conductivity using temperatures measured by the thermocouples.

8. The method of measuring the dynamic thermal conductivity of the micro-structure fluid according to claim 7, wherein an rpm of the rotating plate ranges from 0.1 rpm to 100 rpm.

* * * * *